United States Patent [19]

Vaillancourt

[11] 4,318,402
[45] Mar. 9, 1982

[54] LIQUID INFUSION CATHETER ASSEMBLY

[75] Inventor: Vincent L. Vaillancourt, Livingston, N.J.

[73] Assignee: Critikon, Inc, Tampa, Fla.

[21] Appl. No.: 56,761

[22] Filed: Jul. 12, 1979

[51] Int. Cl.³ .............................................. A61M 5/00
[52] U.S. Cl. ................................................ 128/214.4
[58] Field of Search .................... 128/214.4, 348, 240, 128/241, 350 R, 349

[56] References Cited

U.S. PATENT DOCUMENTS

| 4,016,879 | 4/1977 | Mellor | 128/214.4 |
| 4,149,535 | 4/1979 | Volder | 128/214.4 |
| 4,168,703 | 9/1979 | Kenigsberg | 128/348 |

Primary Examiner—Hiram Bernstein
Attorney, Agent, or Firm—Donal B. Tobin

[57] ABSTRACT

A liquid infusion catheter assembly comprises a hub and a first hollow catheter connected at its proximal end, and being in fluid communication with, the hub. This catheter has at least one fluid outlet opening. A second hollow catheter, extending from, but being out of fluid communication with, the hub surrounds the first catheter with a space therebetween. This second catheter extends distally farther than the first catheter and has at least one hole through its surface where it surrounds the first catheter, and has a fluid outlet opening in the portion extending beyond the first catheter.

6 Claims, 3 Drawing Figures

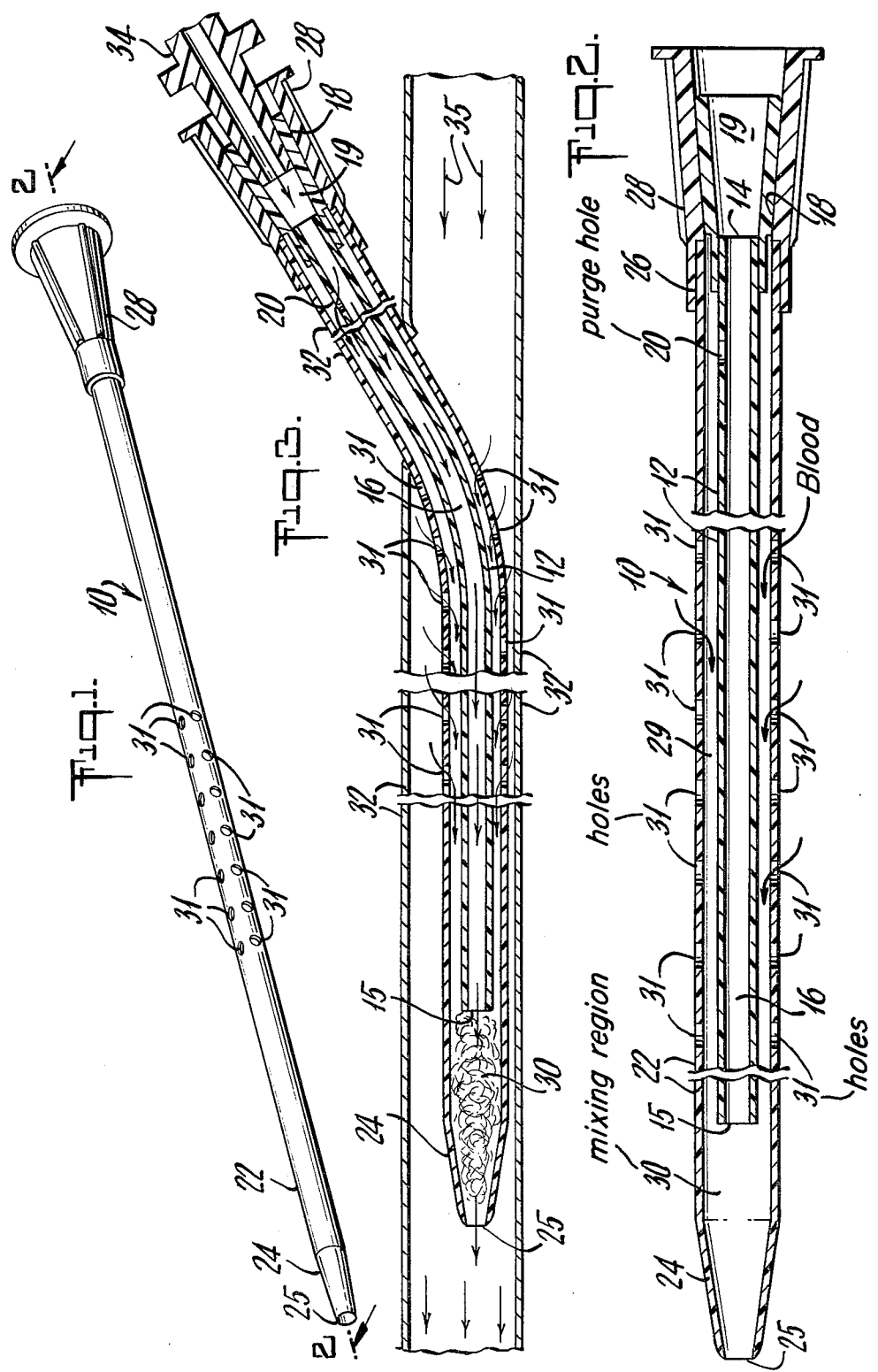

LIQUID INFUSION CATHETER ASSEMBLY

BACKGROUND OF THE INVENTION

The present invention relates to a catheter assembly for delivering liquids to the blood stream of a patient, and more particularly, concerns an infusion catheter assembly constructed to pre-dilute parenteral liquids prior to being delivered to the vein of a patient.

Standard intravenous catheters for delivering parenteral liquids into the blood stream of a patient are generally formed with a single liquid outlet at the catheter tip. If a hypertonic solution, total parenteral nutrition liquid or the like is administered through such a catheter, the blood in the immediate vicinity of the catheter outlet receives this liquid. At this point, the infusion liquid is at its highest concentration and, as a result, may cause some complications. Specifically, depending upon the constituents of the infusion solution, irritation of the vein may ensue, inflammation or swelling is possible along with potential vein necrosis, as well as infusion phlebitis due to the hypertonic nature of the infusion solution. With this in mind, it has become common practice to avoid the peripheral veins as much as possible in administering these types of liquids in order to reduce the incidence of phlebitis. For example, a vein, usually sub-clavian, jugular or other central vein, with a large volume of blood flow is selected to provide rapid dilution of the infusion solution in the area of the outlet. It is appreciated that this practice, the insertion of the catheter into a central vein, is much more difficult than insertion into a peripheral vein, and is potentially more harmful since the incidence of infection and other complications is often greater in the central veins. Accordingly, the need for a catheter to deliver diluted infusion solution, particularly to a peripheral vein, has been established, while the satisfactory fulfillment of that need is still being sought.

An arterial infusion catheter disclosed in U.S. Pat. No. 3,888,249 is directed to a catheter design which seeks to improve the mixing of the medication as it is delivered to the bloodstream. This patented invention relies upon a single flexible catheter tube with one or more slits therein which serve as a one-way valve. However, sufficient positive pressure inside the catheter is needed to inject the diffused medication into the bloodstream of the patient. Also, infusion solution at full concentration may impinge on the vein wall.

Other catheter devices and techniques to pre-dilute the infusion solution as it is delivered to the patient are still in demand, and it is to that end which the present invention is directed.

SUMMARY OF THE INVENTION

An infusion catheter assembly comprises a hub with a first hollow catheter connected at its proximal end to the hub. This catheter is in fluid communication with the hub and includes at least one fluid outlet opening. A second hollow catheter, extending from, but being out of fluid communication with, the hub surrounds the first catheter with a space therebetween. The second catheter extends distally farther than the first catheter. There is at least one hole through the surface of the second catheter where it surrounds the first catheter. Fluid outlet means is provided in the second catheter in the portion which extends beyond the first catheter. In operation, and after the catheter combination is inserted into the vein of a patient, blood enters through the peripheral holes of the second surrounding catheter and mixes with the infusion solution transferred from the hub and the first catheter. This mixing occurs in the portion of the assembly where the second catheter extends beyond the first catheter. This mixture, a mixture of blood and infusion solution, is delivered to the bloodstream from the fluid outlet of the second catheter.

From the structural standpoint, the catheter assembly of the present invention is notably different from prior catheters in a number of respects. For instance, the dual catheter construction with the outer catheter extending longer than the inner catheter provides a region wherein the infusion solution may be diluted before it enters the bloodstream of the patient. As pointed out above, the holes in the outer catheter surrounding the inner catheter allow blood to enter into the space between the catheters so that intermixing of blood and infusion solution can be accomplished, thereby reducing the concentration of infusion solution as it is delivered to the bloodstream. As a result, the present invention, which serves to pre-dilute the infusion solution before delivery to the bloodstream, can be used in the secondary peripheral veins during the infusion procedure. The pre-diluted solution serves to minimize the problems associated with standard catheters which deliver high concentrations of infusion solution to the patient, and particularly reduces the phlebitis potential in the veins.

BRIEF DESCRIPTION OF THE DRAWINGS

FIG. 1 is a perspective view illustrating the preferred infusion catheter assembly of the present invention;

FIG. 2 is a cross-sectional view taken along line 2—2 of FIG. 1; and

FIG. 3 is a cross-sectional view of the catheter assembly of FIG. 1 positioned in the vein of a patient and illustrating the function of the catheter components to provide the pre-dilution of the infusion solution to be delivered to the patient.

DETAILED DESCRIPTION

While this invention is satisfied by the embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings, particularly to FIGS. 1 and 2, there are illustrated a preferred infusion catheter assembly 10 of the present invention. As used herein, the word "proximal" shall mean that portion of an element which, during normal use, would be at a location nearest the operator. For example, during the introduction of an infusion catheter assembly into a patient, the hub would be at the proximal end of the catheter assembly. On the other hand, the point of the catheter would be at a location remote from the proximal end, and this end shall be defined in this specification as the "distal" end.

Catheter assembly 10 includes a slender, elongate hollow cylindrical tube serving as a first catheter 12. Catheter 12 is preferably a solid-wall tubular structure with its proximal end 14 and distal end 15 being open and a lumen 16 extending between the openings. Connected to the proximal end of catheter 12 is a hub 18 which has a receptacle-like cavity 19 communicating with lumen 16 of the first catheter. Hub 18 and cavity 19 are adapted to receive a fitting or the like from an administration set so that fluid may be transferred from the administration set through the catheter assembly and into the patient. To this end, hub 18 is typically a female luer fitting, tapered appropriately to receive a mating male fitting from the administration set. Catheter 12 preferably includes a purge hole 20 through its surface near its proximal end the purpose of which will be described more completely hereinafter.

A second hollow catheter 22 is formed from a slender, elongate hollow cylindrical tube. The tube forming second catheter 22 has a larger inside diameter than that of the first catheter. Distal end 24 of second catheter 22 is tapered inwardly to facilitate insertion of the catheter assembly into the vein of the patient. An opening 25 is included in the distal end of the second catheter. Proximal end 26 of the second catheter is also open. A fitting 28 is connected to the proximal end surface of the second catheter. This fitting 28 is similar in many respects to hub 18 connected to the first catheter, except that it is larger in cross-sectional size than hub 18. Preferably, hub 18 and fitting 28 are sized so that hub 18 can be press fit into fitting 28 to form a tight fitting engagement therewith. Thus, the respective proximal ends of the first and second catheters will both lie in the region of the connected hub and fitting. It can be seen that whereas lumen 16 of the first catheter is in fluid communication with cavity 19 of hub 18, the interior portion of second catheter 22 is not in fluid communication with hub 18. When the first catheter and hub are positioned with the hub press fit into the fitting, it can be seen that there is an annular space 29 between first catheter 12 and second catheter 22. Also, second catheter 22 is preferably longer than first catheter 12 so that the distal end of the second catheter extends beyond the distal end of the first catheter. This forms an intermixing region 30 inside the second catheter between the respective distal ends of the first and second catheters.

In the portion of second catheter 22 which surrounds first catheter 12, there is a plurality of holes 31. These holes are preferably located in the central region of the second catheter, i.e. not too close to either the distal or proximal ends thereof. It is also noted that distal opening 15 in first catheter 12 preferably lies distally farther than any of holes 31 through the surface of the second catheter.

While in no way being strictly limited to any particular material out of which the catheter assembly of the present invention is fabricated, plastic materials are generally preferred. The most preferred materials are polytetrafluoroethylene (PTFE) and fluorinated ethylenepropylene (FEP). Furthermore, it is also desirable to fabricate each of the respective catheters from a flexible material in order to impart sufficient pliancy during use of the assembly to thereby limit trauma to the patient, in addition to realizing manufacturing efficiencies.

FIG. 3 illustrates the preferred infusion catheter assembly as previously described as it may appear during use. One way to introduce this preferred infusion catheter assembly into the vein 32 of a patient is by using an introducer needle in conjunction with second catheter 22. The first catheter and connected hub, at this time, are not positioned inside the second catheter. An introducer needle, however, is used to achieve venipuncture by being positioned inside the second cathether (not shown) so that the needle tip protrudes slightly beyond the distal end of the second catheter. After both the introducer needle and the second catheter are introduced into vein 32, the introducer needle is withdrawn from the proximal end of the second catheter, and then first catheter 12 and hub 18 are inserted into second catheter 22 and fitting 28 so that the hub and the fitting are press fit in tight engagement. A male fitting 34 is then placed into receptacle-like cavity 19 of the hub for delivering infusion solution into the interior of the hub for eventual delivery to the patient.

In FIG. 3, it can be seen that both catheters are slightly bent due to the flexible nature of the preferable catheter material. In addition, the catheters are positioned so that peripheral holes 31 through the second catheter are all within vein 32; this not only eliminates any fluid or blood leakage into the tissue surrounding the vein, but also keeps any undesirable air from getting into the line. In this configuration of the catheter assembly, infusion solution is allowed to enter into lumen 16. Some of the blood 35 travelling in vein 32 enters into annular space 29 through holes 31 in the peripheral surface of the second catheter. The blood which enters into annular space 29 travels distally and mixes with infusion solution being deposited from distal opening 15 in the first catheter in intermixing region 30. This intermixing region, due to the spacing between the respective distal ends of the catheters, serves to allow both infusion solution and blood to become mixed, whereby the concentration of the infusion solution will be reduced. Accordingly, when the mixture exits through distal opening 25 of the second catheter in its diluted form, the vein exposure problems at this point are significantly reduced. The blood in vein 32 accepts the delivery of diluted infusion solution more tolerably than the solution at normal strength and concentrations, so that vein phlebitis and inflammation are minimized.

As pointed out earlier, purge hole 20 is preferably included in first catheter 12; this purge hole serves to prevent blood stagnation in the space above peripheral holes 31 inasmuch as a small amount of infusion solution may leak out of purge hole 20 into annular space 29 and be carried toward the distal ends of the catheters. Alternatively, the purge hole could be positioned through the fitting, if desired in order to provide this small infusion flow capability. In addition, the purge hole may include flow limiting means, such as a sintered polyethylene plug to truly limit this leakage rate.

Thus, there has been provided in accordance with this invention an infusion catheter assembly which allows the delivery of a pre-diluted infusion solution to the vein of a patient at reduced levels of concentration at the delivery point to thereby minimize the incidence of vein phlebitis. Accordingly, the infusion catheter assembly of the present invention may be used in secondary peripheral veins which will substantially improve the infusion procedure.

I claim:

1. An infusion catheter assembly to dilute liquid delivered to the bloodstream comprising: a receptacle-like hub; a first hollow catheter connected at its proximal end to said hub with its lumen being in liquid communication with the interior portion of said hub for the receipt and transferral of liquid from said hub, said first catheter having an open distal end, a second hollow catheter connected by its proximal end to said hub, but being out of liquid communication with the interior of said hub, said second catheter having an open distal end extending beyond the distal end of said first catheter, said second catheter surrounding said first catheter with an annular space therebetween, said second catheter having a plurality of holes through its peripheral surface in a central region thereof, said first catheter being located within said second catheter with the open distal end of said first catheter being further distal than any of said holes, so that blood may enter through said holes, flow over said first catheter, and between said distal open end of said first catheter and the open distal end of said second catheter, mix with liquid transferred from said first catheter, said mixture being delivered to the bloodstream from the open distal end of said second catheter.

2. The catheter assembly of claim 1 wherein both said catheters are made of flexible material.

3. The catheter assembly of claim 1 wherein said first catheter is a solid-wall tubular structure with its ends being open.

4. The catheter assembly of claim 3 wherein said first catheter includes a purge hole through its surface near its proximal end.

5. The catheter assembly of claim 1 wherein the distal end of said second catheter is spaced a sufficient distance beyond the distal end of said first catheter to allow intermixing of the liquid delivered from said first catheter with blood entering through said holes into said space between said respective distal ends.

6. The catheter assembly of claim 1 wherein said second catheter is connected at its proximal end to a fitting, said hub being positioned within said fitting in tight engagement therewith.

* * * * *